US008512306B2

(12) United States Patent
Knapp et al.

(10) Patent No.: US 8,512,306 B2
(45) Date of Patent: Aug. 20, 2013

(54) RADIOPHARMACEUTICAL UNIT DOSE CONTAINER TAMPER EVIDENT SAFETY SEAL

(75) Inventors: Paul M. Knapp, Dublin, OH (US); Thomas G. Ziegenhorn, Arlington Heights, IL (US)

(73) Assignee: Cardinal Health 414, LLC, Dublin, OH (US)

( * ) Notice: Subject to any disclaimer, the term of this patent is extended or adjusted under 35 U.S.C. 154(b) by 643 days.

(21) Appl. No.: 12/357,017

(22) Filed: Jan. 21, 2009

(65) Prior Publication Data

US 2010/0185170 A1 Jul. 22, 2010

(51) Int. Cl.

| | |
|---|---|
| ***A61B 19/00*** | (2006.01) |
| ***A61B 19/02*** | (2006.01) |
| *G21F 5/00* | (2006.01) |
| *G21F 5/015* | (2006.01) |
| *G21F 5/018* | (2006.01) |
| *G21F 5/12* | (2006.01) |

(52) U.S. Cl.

USPC ..................... 604/403; 250/505.1; 250/506.1; 588/259

(58) Field of Classification Search

USPC ................. 604/403; 220/DIG. 34; 206/807; 215/45, 47, 48, 49, 216, 224, 234, 250, 306, 215/901, 201, 228, 230, 235, 247, 273, 295, 215/316; 248/94, 101, 175, 126, 147, 151, 248/154, 163.1, 176.1, 188, 5, 51; 24/16 R, 24/30.5 R, 31 R, 68 R, 437, 442, 305, 163 R, 24/572.1, 706, 703.1

See application file for complete search history.

(56) References Cited

U.S. PATENT DOCUMENTS

| | | | | | |
|---|---|---|---|---|---|
| 110,421 | A | | 12/1870 | Bates | |
| 402,370 | A | | 4/1889 | Walch | |
| 760,879 | A | | 5/1904 | Kunzman | |
| 1,278,385 | A | | 9/1918 | Rickard | |
| 3,339,775 | A | * | 9/1967 | Valentin | 215/291 |
| 3,379,328 | A | | 4/1968 | Plion | |
| 4,280,258 | A | | 7/1981 | Kunze | |
| 4,470,173 | A | * | 9/1984 | Adamson | 24/30.5 P |
| 4,501,049 | A | * | 2/1985 | Adamson | 24/30.5 P |
| 4,588,218 | A | | 5/1986 | Guiler et al. | |
| 4,993,570 | A | * | 2/1991 | Julian et al. | 215/252 |
| 5,056,837 | A | | 10/1991 | Fuehrer | |
| 5,191,992 | A | | 3/1993 | Darley | |
| 5,348,180 | A | | 9/1994 | Shepard | |
| 5,350,372 | A | * | 9/1994 | Ikeda et al. | 604/414 |
| 5,397,012 | A | | 3/1995 | Tison et al. | |
| 5,429,256 | A | * | 7/1995 | Kestenbaum | 215/247 |
| 5,462,182 | A | * | 10/1995 | Opresco | 215/216 |
| 5,519,931 | A | | 5/1996 | Reich | |
| 5,524,945 | A | * | 6/1996 | Georgopoulos et al. | 292/307 A |
| 5,526,853 | A | * | 6/1996 | McPhee et al. | 141/329 |
| 5,853,093 | A | * | 12/1998 | Neiger | 215/237 |
| 5,865,330 | A | * | 2/1999 | Buono | 215/216 |
| 6,158,153 | A | | 12/2000 | Morgan | |
| D436,706 | S | | 1/2001 | Clinton | |
| 6,328,356 | B1 | | 12/2001 | Aichmann | |

(Continued)

*Primary Examiner* — Adam Marcetich
(74) *Attorney, Agent, or Firm* — Arent Fox LLP

(57) ABSTRACT

A tamper evident safety seal includes a first band, a second band and first and second arms connecting the first band and the second band. The seal is positioned around a radiopharmaceutical container and further includes a connector assembly having a connector and a break away portion that, when separated, provides visual evidence that the seal has been broken.

13 Claims, 1 Drawing Sheet

(56) References Cited

U.S. PATENT DOCUMENTS

| | | | | |
|---|---|---|---|---|
| 6,343,819 | B1 * | 2/2002 | Shiozaki | 292/307 R |
| 6,449,808 | B1 | 9/2002 | Zappa et al. | |
| 6,648,313 | B2 | 11/2003 | Navarro | |
| 6,828,509 | B2 | 12/2004 | Ito et al. | |
| 6,854,210 | B2 | 2/2005 | Gunderman | |
| 6,895,712 | B2 | 5/2005 | Gunderman et al. | |
| 7,052,055 | B1 * | 5/2006 | Castro et al. | 292/307 A |
| 7,062,820 | B1 | 6/2006 | Oestreich et al. | |
| 7,246,830 | B2 | 7/2007 | Graves et al. | |
| 2002/0121496 | A1 * | 9/2002 | Thiebault et al. | 215/249 |
| 2005/0062608 | A1 * | 3/2005 | Costa | 340/572.9 |
| 2006/0289541 | A1 | 12/2006 | Boback et al. | |
| 2007/0120701 | A1 * | 5/2007 | Teller | 340/693.9 |
| 2008/0028677 | A1 | 2/2008 | Shelton | |
| 2008/0289372 | A1 * | 11/2008 | Rendon et al. | 70/57.1 |

* cited by examiner

RADIOPHARMACEUTICAL UNIT DOSE CONTAINER TAMPER EVIDENT SAFETY SEAL

BACKGROUND

The present disclosure relates to a safety sealing mechanism used in conjunction with radiopharmaceutical unit dose containers. In the field of nuclear medicine, radioactive materials (known as radiopharmaceuticals) are used in various applications. Typically, radiopharmaceuticals are delivered to a caregiver from an outside pharmacy “pre-loaded” into a syringe. Due to the radioactive nature of such radiopharmaceuticals, great care must be utilized in handling. It is common industry practice for the outside pharmacy to ship the syringe-loaded radiopharmaceutical (or other unit dose format) in a shielded container, referred to as a “radiopharmaceutical pig”. The radiopharmaceutical pig generally consists of a base and a cover that is threadably attachable to the base. For various reasons, it is important for caregivers and/or pharmacies to quickly recognize when a radiopharmaceutical pig has been opened (i.e., the cover unscrewed from the base). One current approach for providing this tamper evident safety feature is by applying a shrink wrap about the radiopharmaceutical pig. To effectuate disassembly of the cover from the base, the shrink wrap must be removed (or at least torn). While viable, this approach entails added manufacturing/handling costs, and caregivers may experience difficulties in removing and/or disposing of the shrink wrap.

SUMMARY

Aspects of the present disclosure relate to a tamper evident seal and method for sealing a radiopharmaceutical container. The seal includes a first band, a second band and a connector assembly adapted to be positioned around the container. First and second arms connect the first band to the second band. The connector assembly includes a connector connecting two ends of the seal together and a breakaway portion provided to separate two ends of the seal so as to provide visual evidence the seal has been broken.

In one embodiment, the first band forms an uninterrupted circle adapted to be positioned around an upper portion of the container and the second band includes the connector assembly and is adapted to be positioned around a lower portion of the container. In a further embodiment, the first arm connects the first band to a first leg of the connector assembly and the second arm connects the first band to a second leg of the connector assembly.

BRIEF DESCRIPTION OF THE DRAWINGS

The accompanying drawings are included to provide a further understanding of embodiments and are incorporated in and constitute a part of this specification. The drawings illustrate embodiments and together with the description serve to explain principles of embodiments. Other embodiments and many of the intended advantages of embodiments will be readily appreciated as they become better understood by reference to the following detailed description. The elements of the drawings are not necessarily to scale relative to each other. Like reference numerals designate corresponding similar parts.

DETAILED DESCRIPTION

In the following Detailed Description, reference is made to the accompanying drawings, which form a part hereof, and in which is shown by way of illustration specific embodiments in which the invention may be practiced. In this regard, directional terminology, such as “top,” “bottom,” “front,” “back,” “leading,” “trailing,” etc., is used with reference to the orientation of the Figure(s) being described. Because components of embodiments can be positioned in a number of different orientations, the directional terminology is used for purposes of illustration and is in no way limiting. It is to be understood that other embodiments may be utilized and structural or logical changes may be made without departing from the scope of the present invention. The following detailed description, therefore, is not to be taken in a limiting sense, and the scope of the present invention is defined by the appended claims.

It is to be understood that the features of the various exemplary embodiments described herein may be combined with each other, unless specifically noted otherwise.

Figure 1:
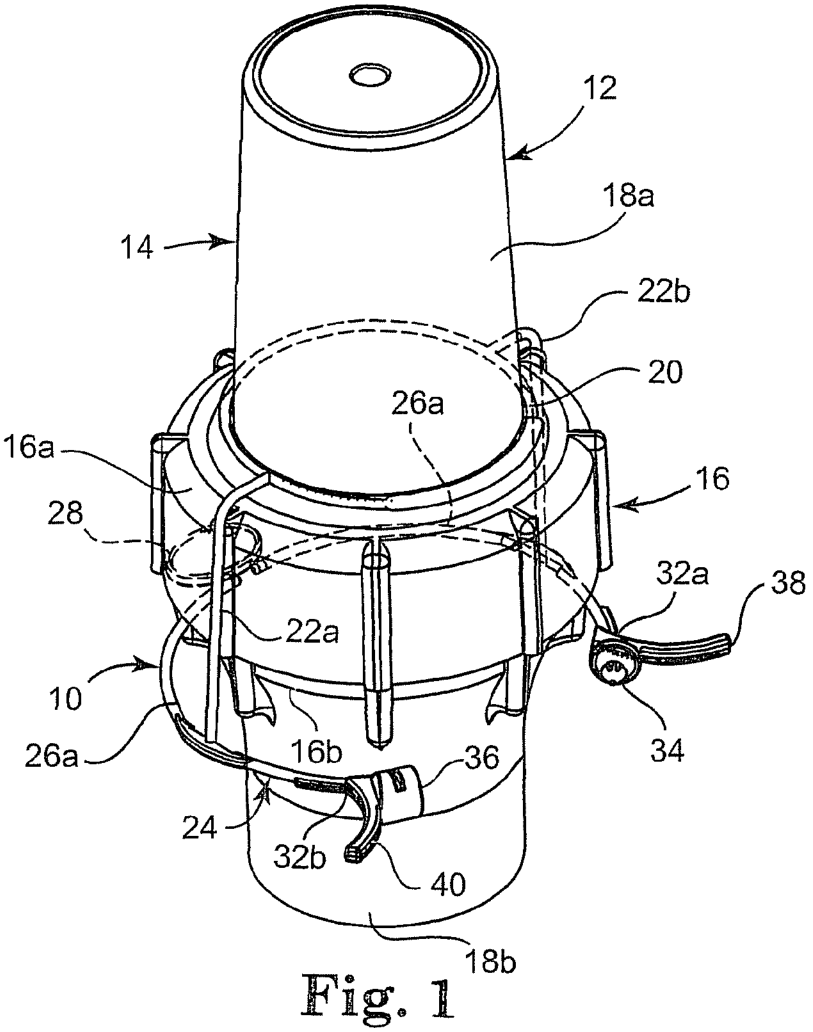
FIG. 1 is a perspective view of an assembly including a safety seal partially assembled to a radiopharmaceutical container.

FIG. 1 illustrates an assembly including a harness or safety seal 10 partially assembled to a radiopharmaceutical container or pig 12. As a point of reference, the radiopharmaceutical pig 12 generally includes (upon final assembly) a tube 14 from which a flange 16 radially projects. The tube 14 includes upper and lower portions 18*a*, 18*b*, with the flange 16 consisting of threadably secured halves 16*a*, 16*b* that are affixed with respect to a corresponding one of the tube portions 18*a*, 18*b*.

Figure 2:
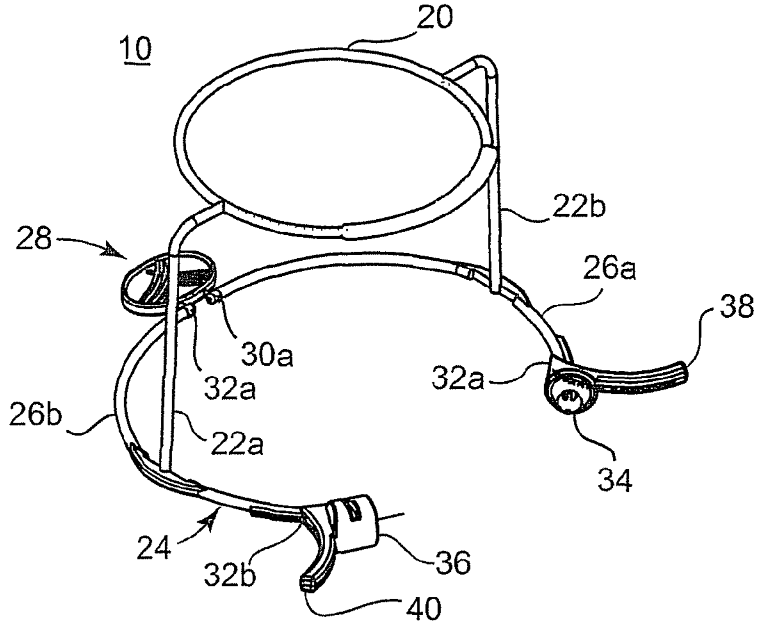
FIG. 2 is a perspective view of the safety seal of FIG. 1.

As further illustrated in FIG. 2, the harness 10 is formed of a flexible, strong material, such as low density polyethylene (LDPE), and defines a first band or ring 20, arms 22*a*, 22*b*, and a second band or ring forming a connector assembly 24. Other types of plastic can also be used, such as polypropylene, high density polyethylene (HDPE), etc. In the embodiment illustrated, the first band 20 is a continuous, uninterrupted circle (or similar shape) having a diameter greater than that of the tube 14, but less than that of the flange 16. The arms 22*a*, 22*b* interconnect the first band 20 with the connector assembly 24. The connector assembly 24 includes opposing legs 26*a*, 26*b*, and a connection tab 28. Leg 26*a* extends between first and second ends 30*a*, 32*a*, whereas leg 26*b* extends between first and second ends 30*b*, 32*b*. Although illustrated wherein the second band forms the connector assembly 24, the connector assembly can be formed in one or more of the other portions of seal 10. For example, the connector assembly can be formed in first band 20, arms 22*a*, 22*b* and/or combinations thereof.

As initially provided, the first ends 30*a*, 30*b* are interconnected by the connection tab 28. The first end 30*a* is connected to a first portion of the tab 28 and spaced apart from the first end 30*b*. The second ends 32*a*, 32*b* are free. In other words, the second ends 32*a*, 32*b* can be moved relative to one another, allowing a diameter collectively defined by the legs 26*a*, 26*b* to be increased or decreased as desired. In this regard, the first leg 26*a* forms a male plug 34, and the second leg 26*b* forms a female receptacle 36 at the corresponding second end 32. The plug 34/receptacle 36 are configured such that the plug 34 can be captured within the receptacle 36, and such that once captured, the plug 34 cannot be removed from the receptacle 36 without destroying the plug 34 (i.e., forming a non-removable connector).

During use, the seal 10 is applied over the radiopharmaceutical pig 12 by sliding the connector assembly 24 and the first band 20 over the tube 14. Due to the extendable nature of the legs 26*a*, 26*b* relative to one another at the second ends 32*a*, 32*b*, the collective diameter of the legs 26*a*, 26*b* can be expanded so as to slide over the flange 16. The first band 20, however, has a diameter less than that of the flange 16, and thus cannot slide beyond the flange 16. Once in the partial assembled position as shown in FIG. 1, the second ends 32*a*, 32*b* are compressed toward one another by a user, causing the plug 34 to be inserted within, and thus by captured by, the receptacle 36. To this end, two grips 38, 40 extend from the second ends 32*a*, 32*b*, respectively, which can be pressed together to secure plug 34 into receptacle 36. In this secured state, an effective diameter of the connector assembly 24 is now less than that of the flange 16. Thus, the harness 10 is "locked" about the flange 16. In this position, the pharmaceutical pig 12 cannot be disassembled (i.e., the flange halves 16*a*, 16*b* cannot be disassembled from one another).

To access pig 12, the seal 10 must first be removed; this is accomplished by breaking the connection tab 28 (e.g., the connection tab 28 is twisted relative to the legs 26*a*, 26*b*). Once broken, the first ends 30*a*, 30*b* can freely be moved relative to one another, allowing a user to displace the legs 26*a*, 26*b* to an effective diameter greater than that of the flange 16. As a result, the user can now slide the seal 10 off of the pharmaceutical pig 12. The removed seal 10 will clearly have the "broken" connection tab 28 (e.g., the connection tab 28 will no longer be connected to one or both of the legs 26*a*, 26*b*), whereas the second ends 32*a*, 32*b* will remain connected to one another. As a result, a visual indication that the pharmaceutical pig has been opened (or at least an attempt was made to open) will be quickly evident.

Although specific embodiments have been illustrated and described herein, it will be appreciated by those of ordinary skill in the art that a variety of alternate and/or equivalent implementations may be substituted for the specific embodiments shown and described without departing from the scope of the present invention. This application is intended to cover any adaptations or variations of the specific embodiments discussed herein. Therefore, it is intended that this invention be limited only by the claims and the equivalents thereof.

What is claimed is:

1. An assembly, comprising:

a radiopharmaceutical container defining a first portion, a second portion and a flange positioned between the first portion and the second portion, wherein the flange comprises a pair of interoperably securable halves, and wherein one of the halves is attached to the first portion and another one of the halves is attached to the second portion; and a tamper evident seal positioned around the radiopharmaceutical container, comprising:

a first band positioned around the first portion of the radiopharmaceutical container;

a second band positioned around the second portion of the radiopharmaceutical container;

first and second arms integral with the first band and the second band and positioned around the flange of the radiopharmaceutical container; and a connector assembly comprising a connector adapted to secure two ends of the seal together and a breakaway portion adapted to separate two ends of the seal in order to provide visual evidence that the seal has been broken and allow access to the container.

2. The assembly of claim 1 wherein the connector includes a plug and a receptacle configured such that the plug is insertable into the receptacle but withdrawal of the plug from the receptacle is not permitted.

3. The assembly of claim 1 wherein the second band comprises first and second legs and wherein the first leg includes a first end coupled to the connector and a second end coupled to the breakaway portion and wherein the second leg includes a first end coupled to the connector and a second end coupled to the breakaway portion.

4. The assembly of claim 3 wherein the breakaway portion comprises a tab having a first portion coupled to the first leg and a second portion, spaced apart from the first portion, coupled to the second leg.

5. The assembly of claim 1 wherein the seal is made of plastic.

6. The assembly of claim 1 wherein the connector includes first and second finger grips.

7. The assembly of claim 1, wherein the flange has a diameter greater than a diameter defined by the first portion and a diameter defined by the second portion.

8. The assembly of claim 1, wherein an end of each of the first and second arms are attached to the second band.

9. A tamper evident safety seal for sealing a radiopharmaceutical container having an upper portion, a lower portion and a flange positioned between the upper portion and the lower portion, the seal comprising:

an upper band positionable around the upper portion of the container, the upper band defining a diameter less than a diameter of the flange;

first and second arms extending from and integral with the upper band, wherein the first and second arms extend about the flange when the upper band is positioned about the upper portion of the container; and a connector assembly integral with the first and second arms and comprising first and second legs configured to jointly circumscribe and contact at least a portion of the container, a connector and a breakaway portion, wherein the first leg is connected to the connector and the breakaway portion and the second leg is connected to the connector and the breakaway portion, and further wherein the connector comprises a plug and a receptacle such that when the plug is inserted into the receptacle the plug is not removable from the receptacle, and further wherein the breakaway portion, when separated from at least a portion of the connector assembly, provides visual evidence that the seal has been broken.

10. The seal of claim 9 wherein the seal is formed of plastic.

11. The seal of claim 9 wherein the connector includes first and second finger grips.

12. The seal of claim 9, wherein the connector assembly defines a diameter less than the diameter of the flange.

13. The seal of claim 9, wherein an end of each of the first and second arms are attached to the connecter assembly.

* * * * *